(12) United States Patent
Chen et al.

(10) Patent No.: US 9,597,406 B2
(45) Date of Patent: Mar. 21, 2017

(54) CONTROLLED RELEASE METHOD FOR A PHARMACEUTICAL COMPOSITION COMPOSED OF CHELATING COMPLEX MICELLES

(71) Applicant: Original BioMedicals Co., Ltd, Tainan (TW)

(72) Inventors: Chia-Hung Chen, New Taipei (TW); Chau-Hui Wang, New Taipei (TW); John-Son Lin, Taipei (TW); Tieh-Hsiung Chiu, Los Angeles, CA (US); Jing-Yi Chen, Taipei (TW); Pi-Hung Liao, Kaohsiung (TW); Chia-Chi Su, Taichung (TW); Wei-Chuan Liao, Kaohsiung (TW)

(73) Assignee: ORIGINAL BIOMEDICALS CO., LTD, Tainan (TW)

( * ) Notice: Subject to any disclaimer, the term of this patent is extended or adjusted under 35 U.S.C. 154(b) by 78 days.

(21) Appl. No.: 14/346,815

(22) PCT Filed: Jan. 31, 2013

(86) PCT No.: PCT/US2013/024049
§ 371 (c)(1),
(2) Date: Mar. 24, 2014

(87) PCT Pub. No.: WO2014/035465
PCT Pub. Date: Mar. 6, 2014

(65) Prior Publication Data
US 2014/0212371 A1    Jul. 31, 2014

Related U.S. Application Data

(60) Provisional application No. 61/694,216, filed on Aug. 28, 2012.

(51) Int. Cl.
| | | |
|---|---|---|
| *A61K 31/74* | (2006.01) | |
| *A61K 47/48* | (2006.01) | |
| *A61K 38/14* | (2006.01) | |
| *A61K 31/164* | (2006.01) | |
| *A61K 31/198* | (2006.01) | |
| *A61K 31/496* | (2006.01) | |
| *A61K 31/661* | (2006.01) | |
| *A61K 31/704* | (2006.01) | |
| *A61K 47/02* | (2006.01) | |
| *A61K 9/107* | (2006.01) | |
| *A61K 9/51* | (2006.01) | |
| *A61K 47/18* | (2006.01) | |
| *A61K 47/22* | (2006.01) | |

(52) U.S. Cl.
CPC ...... *A61K 47/48215* (2013.01); *A61K 9/1075* (2013.01); *A61K 9/5115* (2013.01); *A61K 31/164* (2013.01); *A61K 31/198* (2013.01); *A61K 31/496* (2013.01); *A61K 31/661* (2013.01); *A61K 31/704* (2013.01); *A61K 38/14* (2013.01); *A61K 47/02* (2013.01); *A61K 47/183* (2013.01); *A61K 9/5153* (2013.01); *A61K 47/22* (2013.01)

(58) Field of Classification Search
None
See application file for complete search history.

(56) References Cited

U.S. PATENT DOCUMENTS 7,749,485 B2 *  7/2010  Tournier .............. A61K 9/1075
                                                     424/1.21
7,914,767 B2 *  3/2011  Shankar .............. A61K 9/4858
                                                     424/1.11

OTHER PUBLICATIONS

Frezza, Novel Metals and Metal Complexes as Platforms for Cancer Therapy, Curr Pharm Des. 2010, 16(16), 1813-1815.*
Satoskar, Pharmacology and Pharmacotherapeutics, vol. 1, 1047.*
Flora, Chelation in Metal Intoxication, Int. J. Environ. Res. Public Health, 2010, 7, 2745-2788.*

\* cited by examiner

*Primary Examiner* — Robert A Wax
*Assistant Examiner* — Quanglong Truong
(74) *Attorney, Agent, or Firm* — WPAT, PC; Justin King

(57) ABSTRACT

This invention provides the controlled-release method for a pharmaceutical composition comprising of metals in the drug carrier. The specific chelator is used to trigger the release of active pharmaceutical ingredients from chelating complex micelles. The drug release rate and half-life can also be controlled by manipulating the dosing sequence and the concentration of metal and specific chelator.

18 Claims, 5 Drawing Sheets

CONTROLLED RELEASE METHOD FOR A PHARMACEUTICAL COMPOSITION COMPOSED OF CHELATING COMPLEX MICELLES

BACKGROUND OF THE INVENTION

1. Field of the Invention

The present invention provides the methods for controlling the drug release rate, including administrations of the chelating complex micelles (CCM) that contains at least one drug molecule, one polymer ligand, and one metal core; and at least one selected from: a corresponding metal chelator; and a metal that as the same as the metal core of CCM to control the release rate and concentration of the drugs. The drugs in metal based CCM are therefore released due to the removal of the metal core.

2. Description of the Prior Art

There are several routes to give drugs into the body, either in blood or across the physical fluid. Nonetheless, excess distribution of the drug may result in decreased drug concentration as well as unexpected toxicity in non-target organs or tissues. Consequently, administering more drugs to increase their concentration in the target organ or tissue is necessary. Drug carriers in numerous forms are developed for manipulating water solubility, extending half-life, and changing distribution of drugs in vivo, thus ensuring its efficacy and reducing the adverse effects.

Alterations of the drug dosage may prolong drug release, but cannot provide a better solution for regulating the drug release rate. Prior arts have shown that adjusting pH or altering the temperature of the fluids may accelerate the drug release rate. However, body fluids can only withstand a pH change within the range of 0.1~0.2. Human body temperature is also not suitable for changes more than 2° C. Hence, the clinical applications of these technologies are also limited. It is also difficult to control both distribution and release rate in vivo simultaneously. Prolonging the retention time of drug carriers usually means drugs are released at unexpected time points, which consequently compromise the best drug effects.

Based on the above-mentioned information and to meet the special demands from the industry, the inventor(s) of the present invention, by applying the pharmaceutical composition as claimed in the Taiwan patent (application no. 101128939) filed by the same inventor(s), discloses a chelating complex micelle (CCM) drug carrier comprising at least one metal core, one polymer ligand, and one drug molecule. The CCM not only preserves the potency of the drug, but also prolongs its half-life in vivo as well as specific biodistribution. However, the timing of drug release from CCM also depends on the intrinsic nature of micelles.

SUMMARY OF THE INVENTION

The present invention provides step-by-step methods using a specific metal chelator that corresponds to the metal core of CCM to trigger the release of drugs.

In one aspect, the present invention provides a triggered-release method for manipulating the drug release rate from CCM. Drugs bound on the metal core are released due to the removal of metal, which is chelated by the specific chelator.

The method comprises of the administration of a CCM comprised of at least a drug molecule, a polymer ligand, and a metal core; and at least one selected from: a metal chelator, wherein corresponds to the metal core of chelating complex micelles, and a metal, wherein as the same as the metal core of the chelating complex micelles.

In another aspect, the metal core of CCM as described above is selected from the following group consisting of: Fe, Cu, Ni, In, Ca, Co, Cr, Gd, Al, Sn, Zn, W, Sc, Ti, Mn, As, Y, V, Mg, Be, La, Au, Ag, Cd, Hg, Pd, Re, Tc, Cs, Ir, and Ga.

In the other aspect, the above-mentioned polymer ligand is selected from the group consisting of: poly(ethylene glycol), poly(aspartic acid), poly(glutamic acid), polylysine, poly(acrylic acid), chitosan, polyethyleneimine, poly(methacrylic acid), hyaluronic acid, collagen, poly(N-isopropyl acrylamide), amylose, cellulose, poly(hydroxybutyrate), poly(lactic acid), poly(butylene succinate), polycaprolactone, carboxymethylcellulose, dextran, cyclodextrin, and phospholipid.

In a further aspect, the above-mentioned CCM is selected from at least one of the following group consisting of: liposome, micelle/polymeric micelle, and dendrimer.

Also, the drugs embedded in the CCM are selected from the following group consisting of: amifostine, WR-1065, doxorubicin, pemetrexed, gemcitabine, methotrexate, docetaxel, vinblastine, epirubicin, topotecan, irinotecan, ifosfamide, gefitinib, erlotinib, penicillin class, cloxacillin, dicloxacillin, gentamicin, vancomycin, ciprofloxacin, amphotericin, quinolones, piperazine, fluoroquinolone, nalidixic acid, levofloxacin, trovafloxacin, oseltamivi, metformin, trastuzumab, imatinib, rituximab, bevacizumab, celecoxib, etodolac, ibuprofen, cyclosporine, morphin, erythropoietin, granulocyte colony-stimulating factor, curcumin(enol, keto form), resveratro, piceid, glutathione, vitamin C, acetylcysteine, carnitine, melatonin, tocopherols, tocotrienols (vitamin E), carotenes, ubiquinol, lipoic acid, polyphenols, catecholamine, tempo, asarone, aminoguanidine, tocopherol monoglucoside, glycyrrhizic acid, epicatechin, flavonoid, orientin, vicenin, MPG (2-mercaptopropionylglycine), Mesna (2-mercaptoethanesulfonic acid), galantamine, insulin, imipenem, cilastatin, ertapenem, meropenem, entecavir, telbivudine, rapamycin and lamivudine.

In another aspect, the metal chelator that corresponds to the metal core of CCM drug carrier is selected from the following group consisting of: EDTA (ethylenediaminetetraacetic acid), DTPA (diethylene triamine pentaacetic acid), NTA (nitrilotriacetic acid), detoxamin, deferoxamine, deferiprone, deferasirox, glutathione, metalloprotein, ferrochel (bis-glycinate chelate), ceruloplasmin, penicillamine, cuprizone, trientine, zinc acetate, and dimercaprol.

The time point for administrating the metal chelators is 10 minutes to 12 hours prior to or following administering the CCM.

In the other aspect, the triggered-release method using CCM drug carrier, wherein the metal the same as the metal core of CCM is administered 5 to 180 minutes prior to or following administering the CCM.

In one aspect, the triggered-release method using the CCM as drug carrier wherein the corresponding metal chelator is administered 10 minutes to 12 hours post administering the chelating complex micelles, and the same metal used in the core of chelating complex micelles is then applied to stop or prolong the drug release process.

In another aspect, the triggered-release method of CCM drug carrier, wherein the administration routes of the said metal chelators include oral, intramuscular injection, topical, inhalational, sublingual, subcutaneous injection, inhalation, rectal and ophthalmic administrations.

In another aspect, the present invention also provides a triggered-release method for CCM drug carriers, comprising of the administration of: a chelating complex micelles containing ferrous ion and embedded drug, wherein the drug is amifostine, vancomycin, ciprofloxacin, doxorubicin, or epirubicin, and deferoxamine is administered 0.1 to 24 hours post administration of the chelating complex micelles..

As described in the present invention, the chelating agent traps the metal core of CCM due to their stronger affinity than that between metal and polymer ligand, thus causing the release of drugs. Moreover, the release rate can be regulated by adjusting the chelator concentration and the administration times so as to achieve better efficacy. On the contrary, subsequent administrations of metal ions may extend the time of drug release and slow the release rate induced by chelators. Furthermore, the addition of metal chelator may also reduce the toxicity caused by metal and therefore improve the safety of CCM.

Administration of adequate amount of metal chelators through oral, intramuscular injection, topical, inhalational, oral mucosal, sublingual, subcutaneous injection, nasal, rectal, ophthalmic administrations, blood, lymph, and cerebrospinal fluid prior administration of CCM is expected to release the drugs at the specific organ or tissue. The sequence of administration and its routes can also utilize to regulate the drug release.

Additionally, administration of metal ion before giving CCM can alleviate the dissolution of CCM induced by natural chelators in body, thus resulting in the delayed release behavior of drugs.

BRIEF DESCRIPTION OF THE DRAWINGS

The foregoing summary, as well as the following detailed description of the invention, will be better understood when read in conjunction with the appended drawings. It should be understood; however, that the invention is not limited to the preferred embodiments shown.

DETAILED DESCRIPTION OF THE PREFERRED EMBODIMENT

The present invention will now be described more specifically with reference to the following embodiments, which are provided for the purpose of demonstration rather than limitation.

Figure 1:
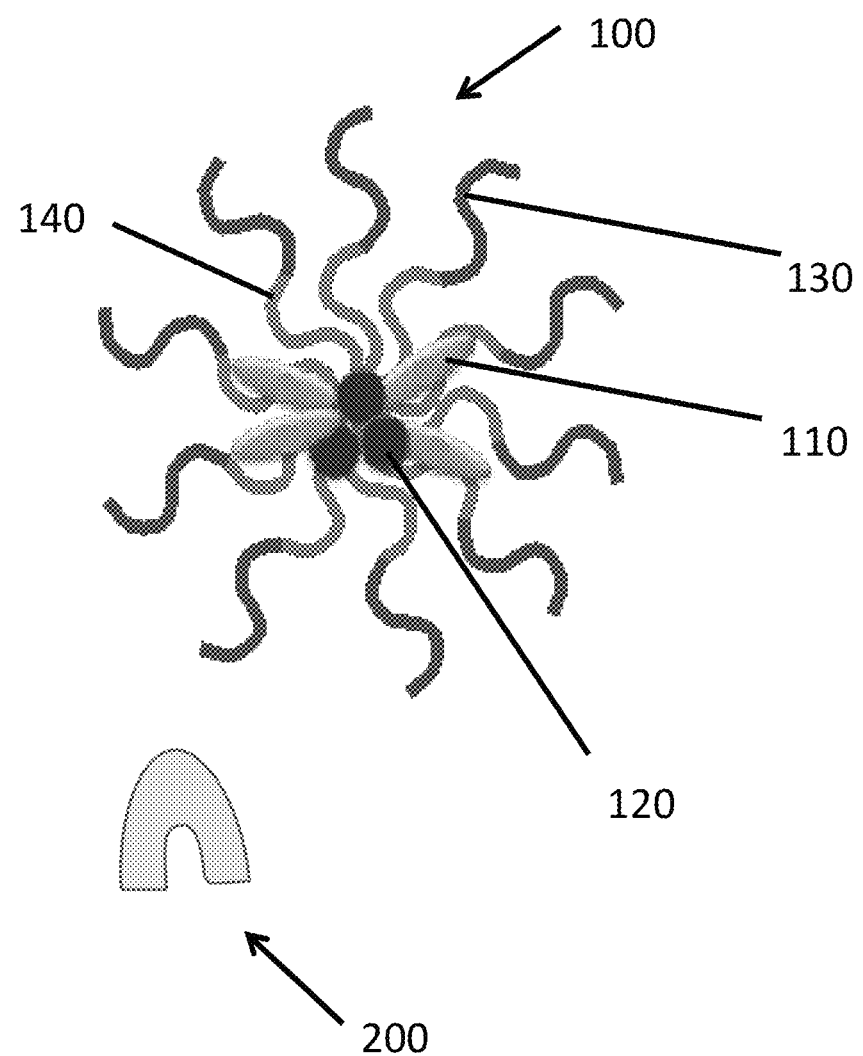
FIG. 1 is the diagram of CCM drug carrier prepared according to the examples described in the embodiment of present invention.
Figure 2:
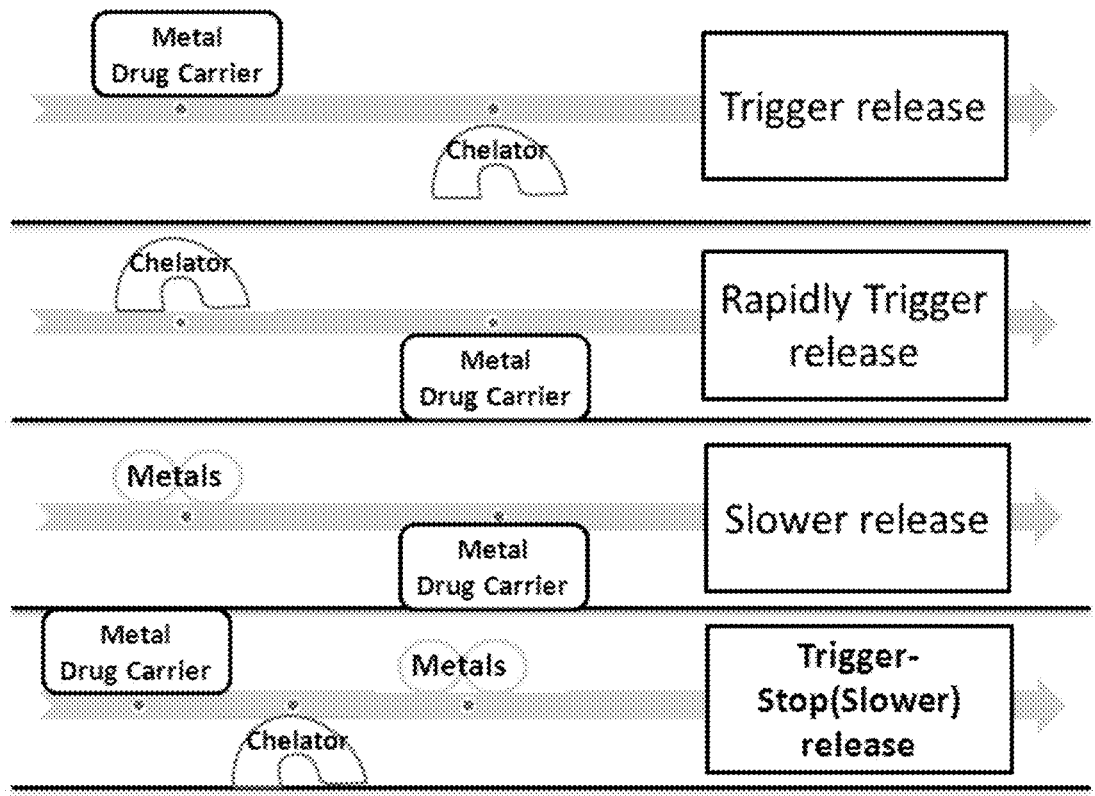
FIG. 2 demonstrates the triggered-release concept of CCM by adding specific metal chelator.

The present invention discloses a controlled-release method for controlling the drug release by use of CCM and its corresponding metal (as shown in FIG. 1), comprising administrations of the CCM drug carrier comprise at least a drug molecule, a metal core and a polymer ligand; and at least one selected from: a corresponding metal chelator; and a metal that as the same as the metal core of CCM. The administration methods include (as shown in FIG. 2):

Trigger-Release: the CCM is given prior to the administration of metal chelator that corresponds to the metal core of CCM. The chelator should be given after the CCM accumulates on the specific location so as to practice target therapy.

Rapidly Trigger-Release: The chelator that corresponds to the metal core of CCM is given before administration of CCM, thus causing fast release of drugs from carriers.

Slower Release: Metal that the same as core of CCM is given prior to the administration of CCM. The competitive inhibition between metal and CCM slows the drug release induced by natural chelator in body.

Trigger-Stop(Slower) Release: The CCM is given prior to the administration of metal chelator that corresponds to the metal core of CCM. The triggered release is then stopped by administering metal that the same as core of CCM. The competitive inhibition between metal and CCM either delays or stops the drug release induced by chelator, which depends on the amount of the existing metal.

EXAMPLE 1

Preparation of the Chelaing Complex Micelles (CCM) Drug Carrier

FIG. 1 shows the diagram of CCM drug carrier. Metals or metal ions are designated as 120. Drugs that can donate lone pairs of electrons are designated as 110. The dispersion segment of (polymer) ligand 130. Polymers or copolymers that can donate an electron pair to the metal are designated as 140. CCM drug carrier 100.

The preparation method used herein is the same as described in another patent filed in Taiwan (application no. 101128939) by the inventor(s) of the present invention, comprising:

1. Amifostine, a compound exhibits antioxidative and anti-free radical activities. It is a precursor of phosphorylated aminothiol, which is converted to an active free thiol metabolite, WR-1065, by alkaline phosphatase in the cells, body fluids and blood Amifostine can protect the cells from radiation and chemical damage, thereby protecting cancer patients from serious adverse effects caused by radiotherapy and chemotherapy.

2. Chelating complex micelles (CCM) drug carrier

The amounts of the reactants used were: 206.44 mg of amifostine, 825.50 mg of PEG-b-PGA (poly(ethylene glycol)-b-poly(glutamic acid)), and 206.44 mg of ferrous chloride $FeCl_2 \cdot 4H_2O$. HEPES (4-(2-hydroxyethyl)-1-piperazinee-thanesulfonic acid) (41.288 mL) buffer solution was introduced with a pH 7.0 at 25° C. and then mixed homogenously and vigorously at 200 rpm. The weight composition of formulation was PEG-b-PGA:$FeCl_2 \cdot 4H_2O$:Amifostine=4:1:1 (w:w:w) with a optimal amifostine reaction concentration at 5 mg/mL. After well mixing in a buffer solution, amifostine, ferrous ion ($Fe^{2+}$) and PEG-b-PGA block copolymer self-assembled to form the complex micelles via coordinate bonding.

Formulation Example 1

| | Weight ratio |
|---|---|
| Amifostine | 1 |
| PEG-b-PGA | 4 |
| Ferrous chloride | 1 |

Formulation Example 2

| | Weight ratio |
|---|---|
| Ciprofloxacin | 1.00 |
| PEG-b-PGA | 5.67 |
| Ferrous chloride | 1.67 |

Formulation Example 3

| | Weight ratio |
|---|---|
| Doxorubicin | 1.00 |
| PEG-b-PGA | 3.40 |
| Ferrous chloride | 0.50 |

Formulation Example 4

| | Weight ratio |
|---|---|
| Vancomycin | 1.00 |
| PEG-b-PGA | 0.60 |
| Ferrous chloride | 0.10 |

Formulation Example 5

| | Weight ratio |
|---|---|
| Epirubicin | 1.00 |
| PEG-b-PGA | 3.40 |
| Ferrous chloride | 0.50 |

EXAMPLE 2

Figure 3:
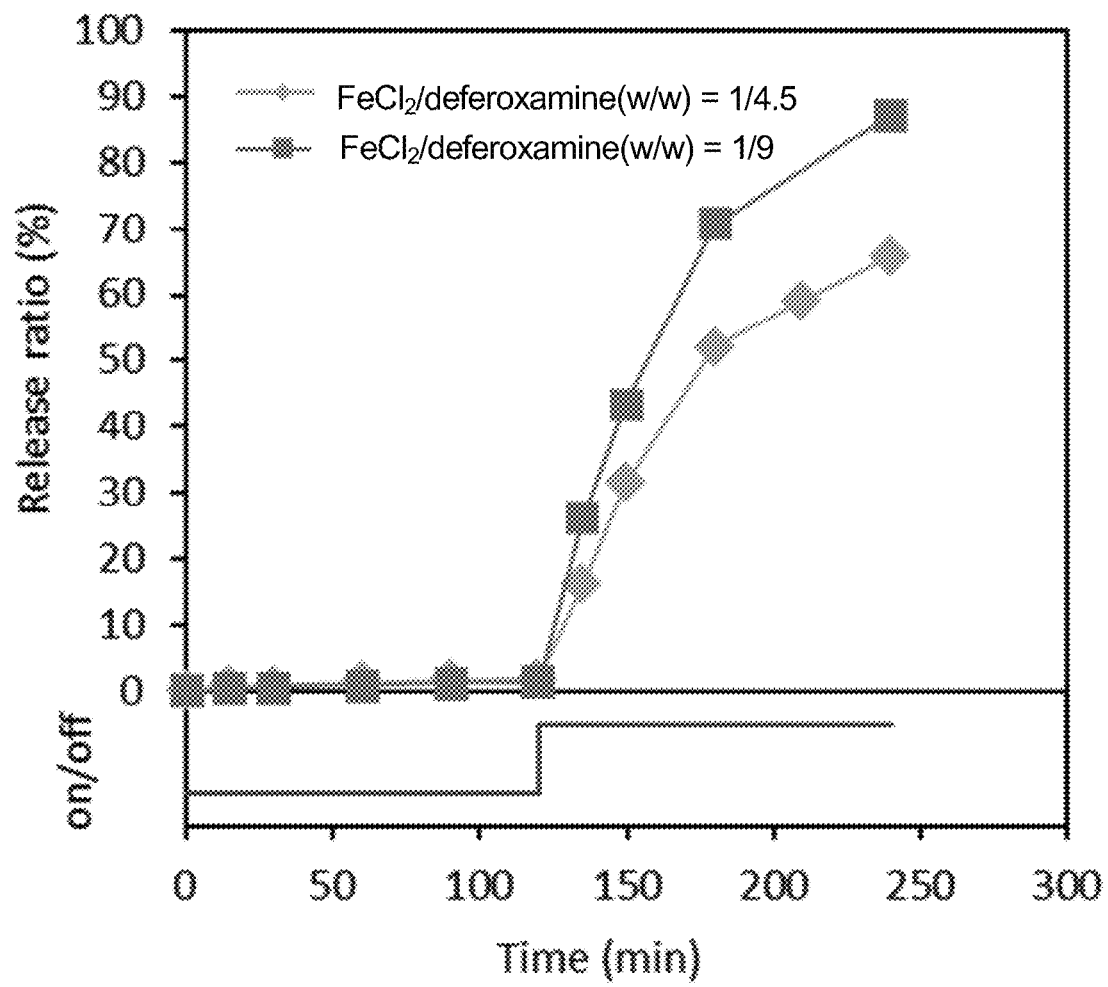
FIG. 3 shows the release profiles of ciprofloxacin-loaded CCM before and after adding iron chelator. Chelator deferoxamine was given separately at 120 min in the amount of 4.5-and 9-fold of ferrous chloride.

Drug Release Rate Before and After Addition of Specific Chelator to CCM Drug Carrier FIG. 1 shows the diagram of CCM drug carrier. Metals or metal ions are designated as 120. Drugs that can donate lone pairs of electrons are designated as 110. The dispersion segment of (polymer) ligand 130. Polymers or copolymers that can donate an electron pair to the metal are designated as 140. CCM drug carrier 100. The corresponding metal chelator 200 is given according to various administration schedules. Example The CCM drug carrier used in this example is ferrous and ciprofloxacin (1 mg/mL) based micelles. The chelator deferoxamine was given at 120 minutes post administration of CCM, with doses 4.5-and 9-fold of ferrous chloride (w/w). As shown in FIG. 3, almost no drug was released before 120 minutes. However, ciprofloxacin CCM showed a pulsed-release after introducing deferoxamine at 120 minutes. The release rate was increased as increasing deferoxamine concentration.

EXAMPLE 3

Spectrophotometric Analysis Before and After Adding Specific Metal Chelator to CCM Drug Carriers In this example, an ELISA reader was used for a full spectrophotometric analysis. Aliquots of each sample including doxorubicin (Dox, 400 μM), FePD (doxorubicin CCM with 400 μM Dox), and FePD+deferoxamine (molar ratio of 1:20) were examined for the OD values at 400-800 nm after stored at room temperature for 4 jours. The data was collected every 2 nm for each sample.

Figure 4:
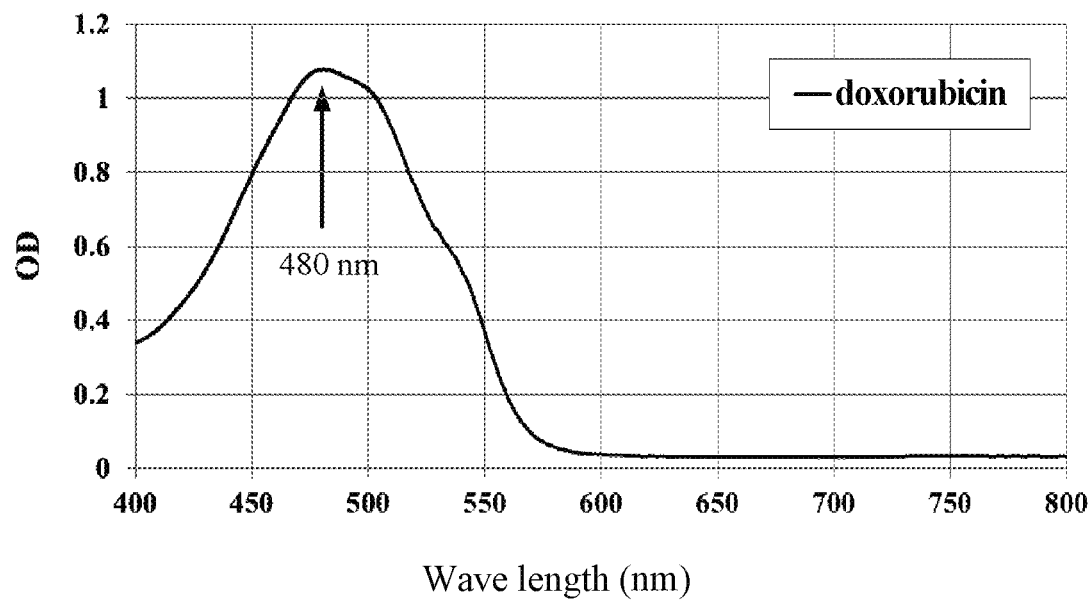
FIG. 4 is the spectrophotometric analysis result of doxorubicin, which shows a significant absorbance at 480 nm
Figure 5:
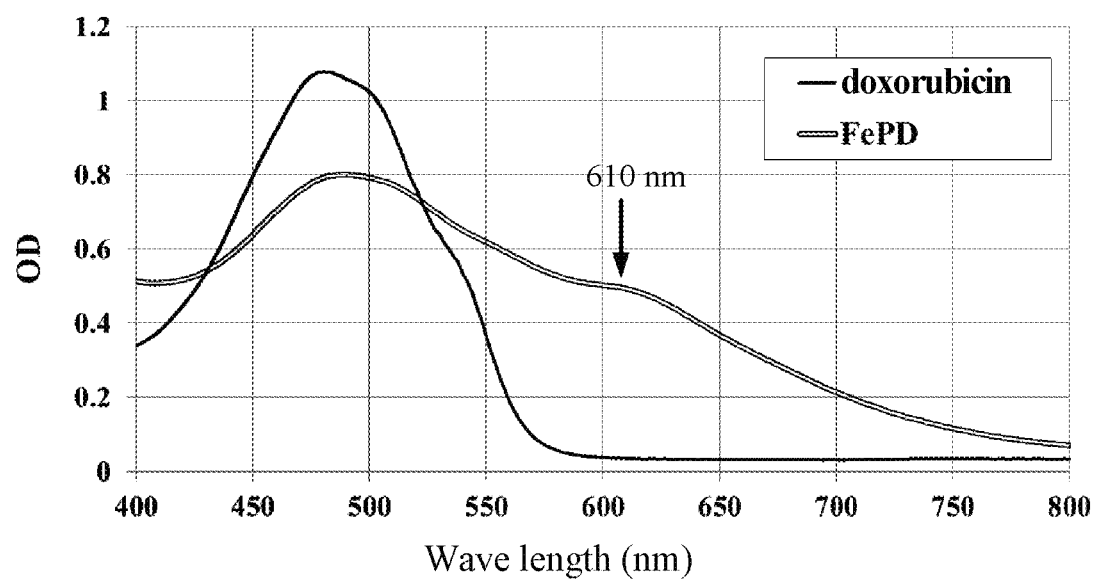
FIG. 5 shows the UV absorbance of doxorubicin and FePD (doxorubicin CCM). A significant absorbance at 610 nm was observed.
Figure 6:
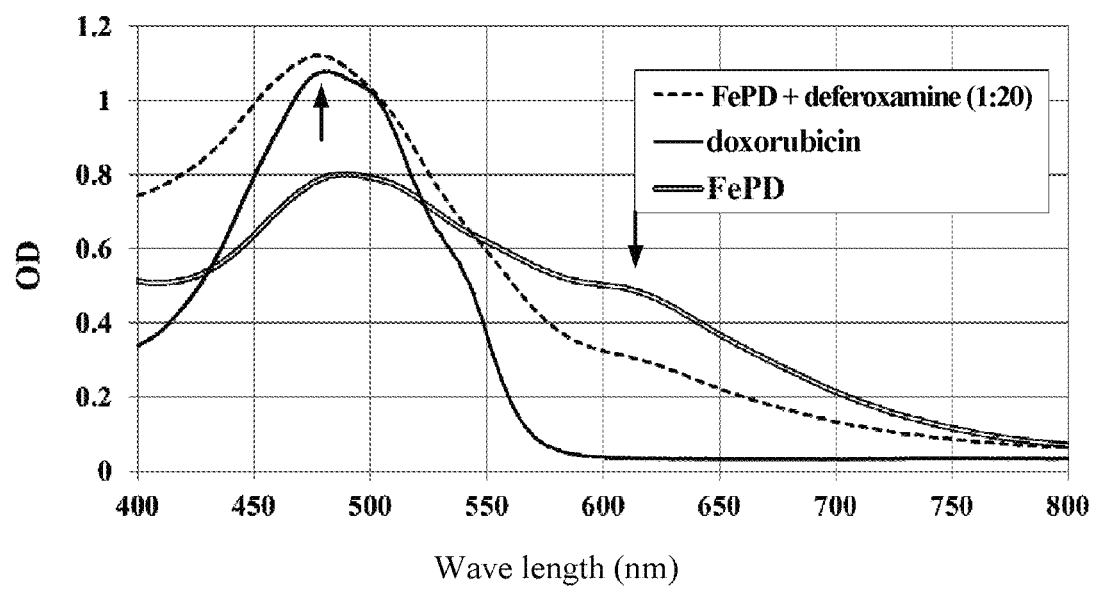
FIG. 6 represents the UV absorbance of doxorubicin, FePD (doxorubicin CCM), and FePD in the presence of 20×deferoxamine, respectively. FePD that reacted with deferoxamine showed significant decrease in absorbance at 610 nm and partial increase at 480 nm.

FIG. 4 is the spectrophotometric analysis results of doxorubicin, which demonstrates apparent absorbance at 480 nm. An absorption peak at 610 nm is observed after coordinate bonding forming between doxorubicin, ferrous ion and PEG-b-PGA (FIG. 5). The intensity of absorbance at 610 nm is significantly decreased after introducing deferoxamine. The increasing intensity of absorption peak at 480 nm also demonstrates that free doxorubicin is released due to the addition of deferoxamine (FIG. 6).

EXAMPLE 4

The cell viability test of doxorubicin CCM (FePD) was examined with and without adding metal chelator deferoxamine. MTT (3-(4,5-cimethylthiazol-2-yl)-2,5-diphenyl tetrazolium bromide) assay was used to assess the cytotoxicity of cells treated with FePD and deferoxamine.

TABLE 1

| Experimental design | |
|---|---|
| Group | Treatment conditions |
| A | NC1 (no treatment) |
| B | NC2 (no serum treatment) |
| C | NC3 (pure water, $H_2O$) |
| D | Doxorubicin (4 μM) |
| E | FePD (4 μM) |
| F | deferoxamine (13.5 μM) |
| G | doxorubicin (4 μM) + deferoxamine (13.5 μM) |
| H | FePD (4 μM) 30 min + deferoxamine (1.35 μM) (1:0.3) |
| I | FePD (4 μM) 30 min + deferoxamine (13.5 μM)(1:3) |
| J | FePD (4 μM) + deferoxamine (1.35 μM) (1:0.3) 30 min |

H&I: Incubation of the cells with FePD for 30 minutes followed by addition of deferoxamine.
J: FePD and deferoxamine were mixed in the test tube for 30 minutes before adding to the cells.

The mouse embryonic liver cells (BNLCL.2) (100 μL) were inoculated onto a 96-well plate with density $1 \times 10^5$ cells/mL and cultured for 24 hr at 37° C. with 5% $CO_2$ before subjecting to the test. After removal of supernatant, 100 μL of each sample was added to the cells and incubated for 2 hours (Table 1). The samples were sterilized by using 0.22 μm filters prior to treating the cells. The plate was then washed with PBS (phosphate buffered saline) and incubated with fresh medium for 24 hours. After removal of supernatant and washed with PBS, 10 μL MTT solution was added to the cells and incubated for 4 hours. The absorbance at 570 nm was measured (BioTek, Synergy TM2, USA).

The in vitro MTT results are shown in Table 2, which indicate that triggered-release method for controlling drug release is feasible. Free doxorubicin (4 μM) showed significant cytotoxicity and consequently the cell viability was relatively low (74.73%). As description mentioned above, FePD exhibited slow-released behavior within 2 hours of incubation. On the contrary, FePD incubated with chelator deferoxamine showed remarked decrease in cell viability, which indicated doxorubicin was released from FePD. Furthermore, the cell viability was decreased as increasing the concentration of deferoxamine.

TABLE 2

| Group | Sample | Cell viability (%) | Standard Deviation |
|---|---|---|---|
| A | NC1 (no treatment) | 113.5240 | 4.2936 |
| B | NC2 (no serum treatment) | 109.2752 | 4.1022 |
| C | NC3 (pure water, $H_2O$) | 100.0000 | 0.6944 |
| D | doxorubicin (4 μM) | 74.7292 | 0.6109 |
| E | FePD (4 μM) | 95.2235 | 0.1238 |
| F | deferoxamine (13.5 μM) | 104.0822 | 0.7510 |
| G | doxorubicin (4 μM) + deferoxamine (13.5 μM) | 78.3115 | 3.4281 |
| H | FePD (4 μM) 30 min + deferoxamine (1.35 μM) (1:0.3) | 91.6412 | 0.1238 |
| I | FePD (4 μM) 30 min + deferoxamine (13.5 μM)(1:3) | 87.3923 | 3.4281 |
| J | FePD (4 μM) + deferoxamine (1.35 μM) (1:0.3) 30 min | 90.8914 | 1.9658 |

In summary, the present invention provides the methods for controlling release of CCM drug carriers. Drugs that can provide lone pairs of electrons such as amifostine, ciprofloxacin, and doxorubicin are examined for triggered-release technology. The methods provided herein are novel and have a remarkable advantage for the drug delivery compared with prior arts, which (1) can control the drug release efficiently in practice, (2) can allow selective distribution of drugs in specific organs, and (3) can manipulate release rate by changing the administration time of metal chelator, CCM, and its corresponding metal.

What is claimed is:

1. A controlled-release method for manipulating drug release, comprising administration of: chelating complex micelles formed via coordinate bonding comprises at least a drug molecule that donates lone pairs of electrons, a polymer ligand that donates an electron pair to a metal core which is Fe; and administration of a metal chelator that corresponds to the metal core of chelating complex micelles, wherein said metal chelator is administered 10 minutes to 12 hours following administering the chelating complex micelles.

2. The method of claim 1, wherein the polymer ligand is selected from the following group consisting of: poly(ethylene glycol), poly(ethylene glycol)-b-poly(glutamic acid) and poly(glutamic acid).

3. The method of claim 1, wherein the drug molecule is selected from the group consisting of: amifostine, WR-1065, doxorubicin, epirubicin vancomycin, and ciprofloxacin.

4. The method of claim 1, wherein the metal chelator that corresponds to the metal core of chelating complex micelles is selected from the following group consisting of: EDTA (ethylenediaminetetraacetic acid), NTA (nitrilotriacetic acid), detoxamin, deferoxamine, deferiprone, deferasirox, glutathione, metalloprotein, ferrochel (bis-glycinate chelate), ceruloplasmin, penicillamine, cuprizone, trientine, zinc acetate, and dimercaprol.

5. The method of claim 1, wherein the administration routes of the metal chelator comprise oral, intramuscular injection, topical, inhalational, sublingual, subcutaneous injection, nasal, rectal and ophthalmic administration.

6. A controlled-release method using chelating complex micelles, comprising administration of: chelating complex micelles containing ferrous ion and embedded drug, wherein the drug is amifostine, vancomycin, ciprofloxacin, doxorubicin, or epirubicin; and deferoxamine is administered 0.1 to 24 hours post administration of the chelating complex micelles.

7. A controlled-release method for manipulating drug release, said method comprising administration of chelating complex micelles formed via coordinate bonding comprises at least a drug molecule that donates lone pairs of electrons, a polymer ligand that donates an electron pair to a metal core which is Fe; and further administering a metal chelator that corresponds to the metal core of the chelating complex micelles wherein the metal chelator is administered 10 minutes to 12 hours prior to administration of the chelating complex micelles.

8. The method of claim 7, wherein the polymer ligand is selected from the following group consisting of: poly(ethylene glycol), poly(ethylene glycol)-b-poly(glutamic acid) and poly(glutamic acid).

9. The method of claim 7, wherein the drug molecule is selected from the group consisting of: amifostine, WR-1065, doxorubicin, epirubicin vancomycin, and ciprofloxacin.

10. The method of claim 7, wherein the metal chelator that corresponds to the metal core of chelating complex micelles is selected from the following group consisting of: EDTA (ethylenediaminetetraacetic acid), NTA (nitrilotriacetic acid), detoxamin, deferoxamine, deferiprone, deferasirox, glutathione, metalloprotein, ferrochel (bis-glycinate chelate), ceruloplasmin, penicillamine, cuprizone, trientine, zinc acetate, and dimercaprol.

11. A controlled-release method for manipulating drug release, said method comprising administration of chelating complex micelles formed via coordinate bonding comprises at least a drug molecule that donates lone pairs of electrons, a polymer ligand that donates an electron pair to a metal core which is Fe; and further administering a metal that is the same as the metal core of the chelating complex micelles wherein the metal is administered 5 minutes to 180 minutes prior to administration of the chelating complex micelles.

12. The method of claim 11, wherein the polymer ligand is selected from the following group consisting of: poly(ethylene glycol), poly(ethylene glycol)-b-poly(glutamic acid) and poly(glutamic acid).

13. The method of claim 11, wherein the drug molecule is selected from the group consisting of: amifostine, WR-1065, doxorubicin, epirubicin vancomycin, and ciprofloxacin.

14. The method of claim 11, wherein the metal chelator that corresponds to the metal core of chelating complex micelles is selected from the following group consisting of: EDTA (ethylenediaminetetraacetic acid), NTA (nitrilotriacetic acid), detoxamin, deferoxamine, deferiprone, deferasirox, glutathione, metalloprotein, ferrochel (bis-glycinate chelate), ceruloplasmin, penicillamine, cuprizone, trientine, zinc acetate, and dimercaprol.

15. A controlled-release method for manipulating drug release, said method comprising administration of chelating complex micelles formed via coordinate bonding comprises at least a drug molecule that donates lone pairs of electrons, a polymer ligand that donates an electron pair to a metal core which is Fe; and further administering a metal chelator that corresponds to the metal core of the chelating complex micelles and a metal that is the same as the metal core of the chelating complex micelles wherein the metal chelator is administered 10 mins to 12 hours post administration of the chelating complex micelles and the metal is administered following the administration of the metal chelator to stop or prolong the drug release process.

16. The method of claim 15, wherein the polymer ligand is selected from the following group consisting of: poly(ethylene glycol), poly(ethylene glycol)-b-poly(glutamic acid) and poly(glutamic acid).

17. The method of claim 15, wherein the drug molecule is selected from the group consisting of: amifostine, WR-1065, doxorubicin, epirubicin vancomycin, and ciprofloxacin.

18. The method of claim 15, wherein the metal chelator that corresponds to the metal core of chelating complex micelles is selected from the following group consisting of: EDTA (ethylenediaminetetraacetic acid), NTA (nitrilotriacetic acid), detoxamin, deferoxamine, deferiprone, deferasirox, glutathione, metalloprotein, ferrochel (bis-glycinate chelate), ceruloplasmin, penicillamine, cuprizone, trientine, zinc acetate, and dimercaprol.

\* \* \* \* \*